US00PP25509P3

(12) United States Plant Patent
Schoone

(10) Patent No.: US PP25,509 P3
(45) Date of Patent: May 5, 2015

(54) *PHALAENOPSIS* ORCHID PLANT NAMED 'GYPSY QUEEN'

(50) Latin Name: *Phalaenopsis hybrida*
Varietal Denomination: Gypsy Queen

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 14 days.

(21) Appl. No.: 13/986,270

(22) Filed: Apr. 18, 2013

(65) Prior Publication Data

US 2013/0291243 P1 Oct. 31, 2013

Related U.S. Application Data

(60) Provisional application No. 61/638,438, filed on Apr. 25, 2012.

(30) Foreign Application Priority Data

Apr. 26, 2012 (NL) ..... PBS OPS900

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP; Sunit Talapatra

(57) ABSTRACT

A new and distinct *Phalaenopsis* plant named 'Gypsy Queen' particularly characterized by flowers which are purple/violet with purple stripes; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Gypsy Queen'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Gypsy Queen'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Gypsy Queen' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Gypsy Queen' originated from a cross made by the inventor in 1999 in Strengweg, Heemskerk, The Netherlands. The female or seed parent is the *Phalaenopsis* cultivar designated 'Happy Valentine', unpatented. The male or pollen parent is the *Phalaenopsis* cultivar designated 'Sweet Melody', unpatented. The new *Phalaenopsis* 'Gypsy Queen' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Gypsy Queen', which in combination distinguish this *Phalaenopsis* as a new and distinct cultivar:

1. flowers which are purple/violet with purple stripes;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Gypsy Queen', the female parent 'Happy Valentine' has dark pink flowers and the male parent 'Sweet Melody' has striped pink colored flowers, whereas the flowers of 'Gypsy Queen' are purple/violet with purple stripes.

Presently, the most commercially similar cultivars to the claimed cultivar 'Gypsy Queen' are the parent cultivars 'Happy Valentine' and 'Sweet Melody', to which a comparison has been provided above.

BRIEF DESCRIPTION OF THE PHOTOGRAPHS

The accompanying photographs illustrate the overall appearance of the new *Phalaenopsis* 'Gypsy Queen' showing the colors as true as is reasonably possible with colored reproductions of this type. Colors in the photographs may differ slightly from the color values cited in the detailed botanical description, which accurately describe the color of 'Gypsy Queen'.

DETAILED BOTANICAL DESCRIPTION

Figure 1:
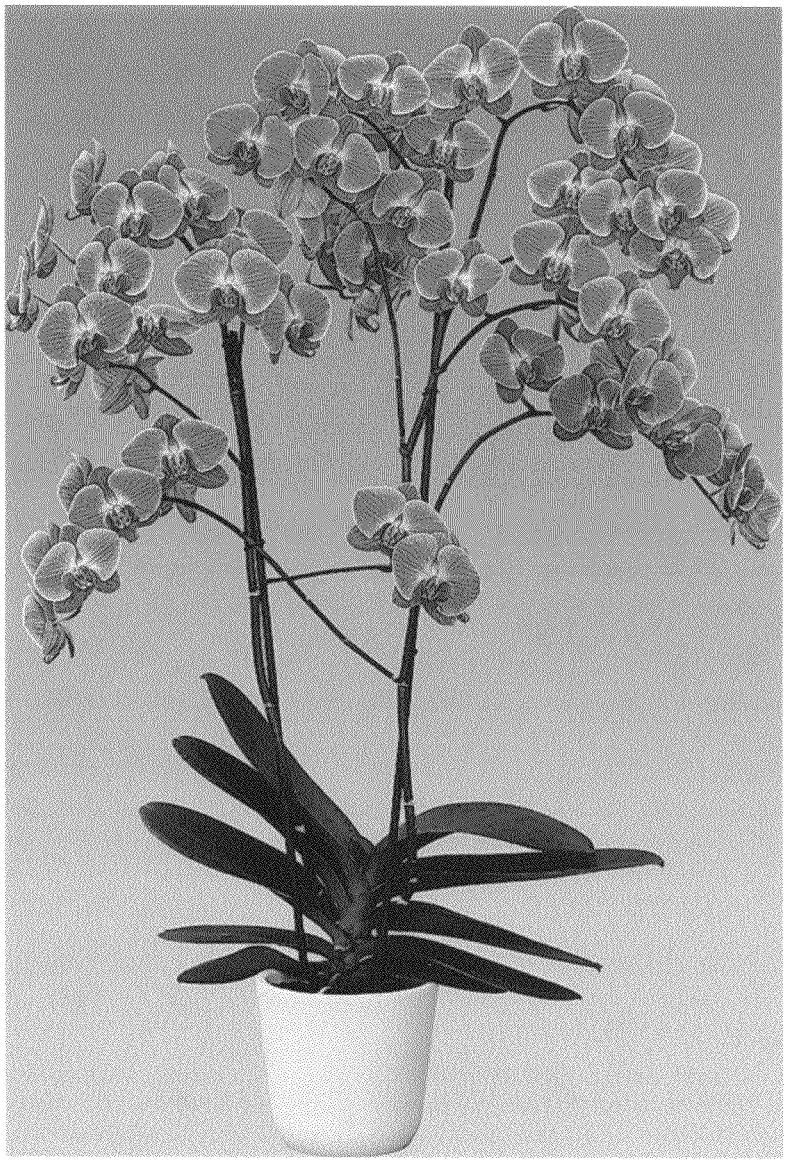
FIG. 1 shows a side view perspective of a typical flowering plant of 'Gypsy Queen' in a 12 cm pot, at 16 months of age.

The new *Phalaenopsis* cultivar 'Gypsy Queen' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Gypsy Queen' as grown in a greenhouse in Strengweg, Heemskerk, The Netherlands, under conditions which closely approximate those generally used in commercial practice. Initially, the ideal temperature to grow plants of 'Gypsy Queen' is 27° C. during the day and at night. Then, during the flowering phase of 'Gypsy Queen', the ideal growing temperature is 20-22° C. during the day and 18° C. at night. Light levels for growing 'Gypsy Queen' are a minimum of 5,000 lux and a maximum of 10,000 lux. A balanced fertilizer with level of 200 ppm N, 87 ppm P, 168 ppm K is applied. Duration of growth of 'Gypsy Queen' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Gypsy Queen' plants described is 12 months after potting.

Classification:

*Botanical.—Phalaenopsis hybrida.*

Parentage:

*Female or seed parent.—Phalaenopsis* cultivar designated 'Happy Valentine', unpatented.

*Male or pollen parent.—Phalaenopsis* cultivar designated 'Sweet Melody', unpatented.

Propagation:

*Type.*—Tissue culture (mericloning).

*Rooting habit and description.*—Fleshy; approximately 3 mm-7 mm wide and yellow/green in color (RHS 144A); freely branching. It takes 12 weeks for plants growing in tissue culture to initiate roots.

Plant:

*Size at maturity.*—Height (from bottom of pot to the highest flower): about 68 cm. Spread: about 60 cm.

*Growth habit.*—Standard; dark green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt.

*Texture (upper & underside).*—Smooth and leathery.

*Pubescence.*—None.

*Mature leaf length.*—About 14 to 23 cm.

*Mature leaf width.*—About 6 to 11 mm.

*Mature leaf thickness.*—About 1.5 mm.

*Mature leaf color.*—Upper side: green (RHS N137B). Under side: yellow/green (RHS 146B) some have red/purple edges (RHS 59A).

*Leaf base.*—Acute.

*Margin.*—Entire.

*Venation.*—Pattern: parallel. Color of midvein: upper side: green (RHS N137A). Under side: yellow/green (RHS 146C).

Raceme:

*Quantity per plant.*—About 2.

*Number of flowers per raceme.*—About 8 to 20.

*Length.*—About 65 cm.

*Diameter.*—About 6 mm.

*Strength.*—Strong.

*Aspect.*—Upright.

*Texture.*—Glabrous and smooth.

*Color.*—At the bottom purple (RHS N77A) and some RHS 146B. Closer to the top RHS 146B and some RHS N77A.

*Internode.*—Length: about 30 to 45 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 21 mm to 25 mm. Diameter (at midpoint): about 15 mm to 22 mm. Shape: egg-shaped/oval. Color: Main color is purple (RHS 77A) at the base some green/yellow (RHS 145B) and violet stripes (RHS 86A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
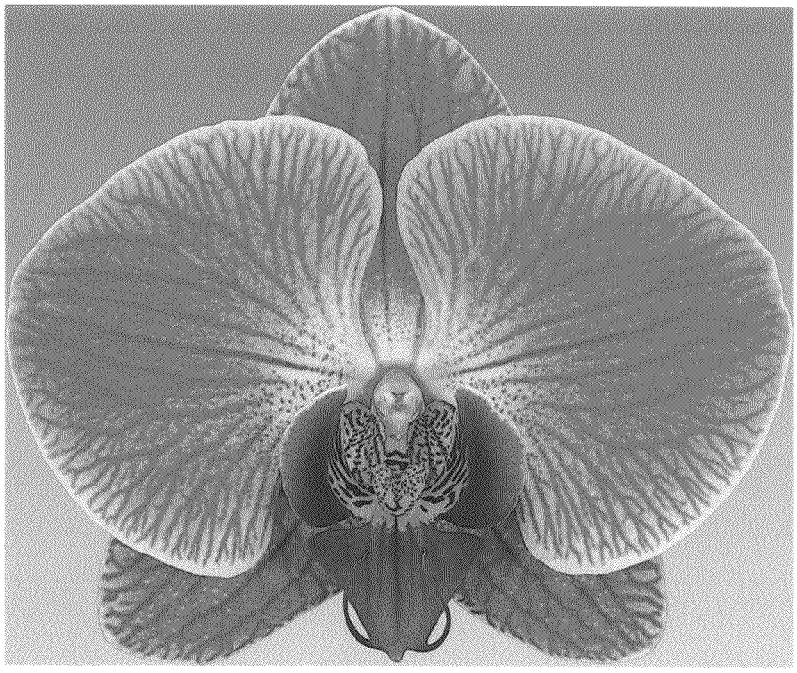
FIG. 2 shows a close-up view of the typical flower of 'Gypsy Queen'.
Figure 3:
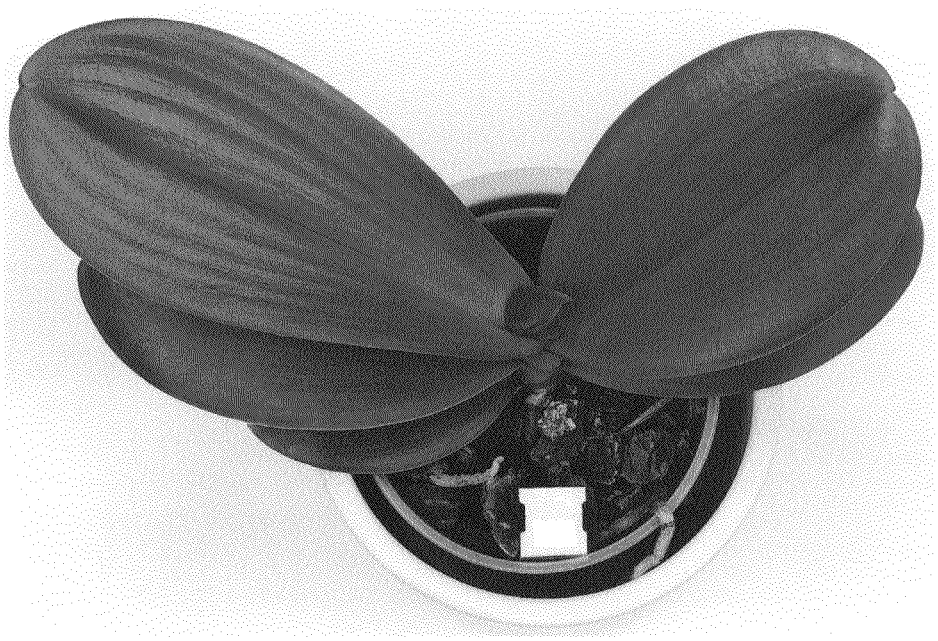
FIG. 3 shows a close-up view of the typical leaves of 'Gypsy Queen'.

*Flower*.—Rate of opening: Flowers fully opened about 2 to 3 days after petal and sepal separation. Orientation at opening: slanted upward and outward. Shape: Typical shape of *Phalaenopsis* Orchid; see FIG. 2. Size (of single bloom): Height: about 60 mm to 80 mm. Diameter: about 67 mm to 95 mm.

*Petals*.—Quantity and arrangement: three petals and three sepals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: oval. Margin: entire and weakly undulate. Base: broadly ovate. Length: about 45 mm. Width: about 35 mm. Texture: Upper surface: smooth and satiny. Under surface: smooth and satiny. Color (when fully opened): upper side: Main color is purple/violet (RHS N80A). Base and edges are white (RHSNN155C). At the base some purple stripes/spots (RHS N80A and RHS 77A). Under side: edges and base are a white (RHS NN155C). Main color is purple/violet (RHS N80A) and purple/violet stripes (RHS N81A). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire. Apex: oval. Length: about 21 mm. Width (not flattened): about 20 mm. Depth of tube (made from lateral lobes): about 15 mm. Texture: Upper and under surface: smooth and satiny. Color (when fully opened): Midlobe: upper surface: Main color is red/purple (RHS 72A). At the base some yellow (RHS 9A) and in the center a purple vein (RHS 79A). Under surface: main color is purple (RHS 77A), left and right red/purple (RHS 71A) in the center some purple (RHS 77B) and at the end a small spot of white (RHS NN155C). Lateral lobes: upper surface: base and edges are white (RHS NN155C) upper edge at base yellow (RHS 9A). Then red/purple (RHS 59A) which runs into purple (RHS 77A) . Under surface: main color is purple/violet (RHS N80A). Base and edges are white (RHS NN155C) with small stroke of yellow (RHS 9D). At the end some red/purple (RHS 59A). Cirrhi: about 18 mm, long and a little bit curly at the end with point in the middle color: purple (RHS 79B) with white tips (RHS NN155C). Pestle (Callosities): Length: about 7 mm. Width (not flattened): about 6 mm. Color: white on the sides and a little bit inside (RHS NN155C). Edges and V notch yellow (RHS 9A) with red/purple spots/stripes (RHS 59A).

*Sepals*.—Arrangement: Outer whorl comprises 3 sepals. Overall shape: egg-shaped and weakly cupped. Margin: entire and weakly undulate. Length: about 38 mm. Width: about 30 mm. Apex: oval with small point. Texture: bold and light curly. Upper and under surface: smooth and satiny. Color (when fully opened): upper side: Main color dorsal sepal is purple/violet (RHS N80A). the base and a small edge are white (RHS NN155C). Stripes are purple (RHS 77A). Main color lateral sepals is RHS N80A. Base and edges are white (RHS NN155C). Stripes are purple (RHS 77A). From the base a vague yellow/green mark (RHS 150D) and some red/purple spots (RHS 72A). Under side: dorsal at the base thin white edge (RHS NN155C). Main color is purple (RHS 77B) with red/purple stripes (RHS 72A). At the lateral sepals there is at the base also a vague yellow/green mark (RHS 145D).

*Pedicel*.—Length: about 32 mm. Diameter: about 3 mm. Texture: glabrous and smooth. Color: green (RHS N137A) to yellow/green (RHS 145C) and red/purple (RHS 59A) to red/purple (RHS 62D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 11 mm. Diameter: about 6 mm. Color: purple/violet (RHS N80A).

*Pollinia*.—Quantity: two. Diameter: about 1 mm. Color: orange (RHS 25A).

*Ovary*.—Length: about 4 mm. Diameter: about 6 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Gypsy Queen', as illustrated and described herein.

* * * * *